(12) United States Patent
Hallinan et al.

(10) Patent No.: US 10,227,283 B2
(45) Date of Patent: Mar. 12, 2019

(54) REACTION CONTROL IN ACETIC ACID PROCESSES

(71) Applicant: LyondellBasell Acetyls, LLC, Houston, TX (US)

(72) Inventors: Noel C. Hallinan, Loveland, OH (US); John D. Hearn, Beach City, TX (US); Ryan J. Mathews, Tomball, TX (US); Brian A. Salisbury, Beach City, TX (US); Daniel F. White, Houston, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 0 days.

(21) Appl. No.: 16/022,121

(22) Filed: Jun. 28, 2018

(65) Prior Publication Data

US 2019/0002386 A1 Jan. 3, 2019

Related U.S. Application Data

(60) Provisional application No. 62/527,526, filed on Jun. 30, 2017.

(51) Int. Cl.
*C07C 51/12* (2006.01)
(52) U.S. Cl.
CPC .................. *C07C 51/12* (2013.01)
(58) Field of Classification Search
CPC .................................................. C07C 51/12
See application file for complete search history.

(56) References Cited

U.S. PATENT DOCUMENTS

| 4,792,620 | A | * | 12/1988 | Paulik | B01J 31/0231 |
| | | | | | 560/232 |
| 6,103,934 | A | | 8/2000 | Hallinan et al. | |
| 6,362,366 | B1 | | 3/2002 | Hallinan et al. | |
| 6,552,221 | B1 | | 4/2003 | Hallinan et al. | |
| 7,390,919 | B1 | * | 6/2008 | Salisbury | C07C 29/88 |
| | | | | | 560/248 |
| 8,519,182 | B2 | | 8/2013 | Salisbury et al. | |
| 8,629,298 | B2 | | 1/2014 | Salisbury et al. | |
| 2012/0095259 | A1 | * | 4/2012 | Salisbury | C07C 51/12 |
| | | | | | 562/519 |
| 2013/0345474 | A1 | * | 12/2013 | Hallinan | C07C 51/50 |
| | | | | | 562/608 |
| 2016/0264502 | A1 | | 9/2016 | Hallinan et al. | |

FOREIGN PATENT DOCUMENTS

WO 0037405 A1 6/2000
WO 2016144870 A1 9/2016

OTHER PUBLICATIONS

Norskov et al, Nature Chemistry, Towards the Computational Design of Solid Catalysts, 2009, 1, pp. 37-46. (Year: 2009).*
The International Search Report and Written Opinion for PCT/US2018/040061 dated Oct. 16, 2018.

* cited by examiner

*Primary Examiner* — Paul A Zucker

(57) ABSTRACT

The present disclosure provides for a method for measuring the concentration of one or more components in a feed stream or reactor mixture of a process for producing acetic acid by both infrared and Raman spectroscopic analyses. In some embodiments, at least one feed stream comprising water is adjusted in response to the measured concentration of one or more components.

20 Claims, 3 Drawing Sheets

US 10,227,283 B2

REACTION CONTROL IN ACETIC ACID PROCESSES

CROSS-REFERENCE TO RELATED APPLICATIONS

This application claims the benefit of priority to U.S. Provisional Patent Application No. 62/527,526 filed on Jun. 30, 2017, which is incorporated herein by reference in its entirety.

FIELD OF THE INVENTION

The present disclosure generally relates to processes for producing acetic acid. In particular, embodiments contained herein relate to measuring a concentration of one or more components in the process and achieving or maintaining water in a desired concentration range in the reactor mixture in such processes.

BACKGROUND OF THE INVENTION

Acetic acid is commercially produced from methanol and carbon monoxide by methanol carbonylation in the presence of water. The process may further contain methyl acetate as a co-feed. As an alternative to methyl acetate as a co-feed, the reaction can take place in the presence of a mixture of methyl acetate and methanol from byproduct streams of the hydrolysis/methanolysis of polyvinyl acetate. Various techniques can be used to determine the components of the reaction mixture and to modify the process.

SUMMARY OF THE INVENTION

The present disclosure provides a method for measuring the concentration of one or more components in a feed stream or reactor mixture of an acetic acid process by both infrared and Raman spectroscopic analyses and adjusting at least one water feed stream to the acetic acid reactor mixture in response to the measured concentration. In embodiments of this disclosure, real time measurement of concentrations of a feed stream component and/or a reactor mixture component permits better control of the amount of water in the acetic acid reactor. In addition, embodiments of this disclosure provide direct measurement of a feed stream, which permits the finding of fluctuations in the feed stream into the acetic acid reactor, so that negative effects on process in the reactor due to the fluctuations can be minimized.

In a general embodiment, the present disclosure provides a method for producing acetic acid comprising: A) combining, in a carbonylation reactor, a carbonylation catalyst, methanol, carbon monoxide, and water, to form a reactor mixture; B) introducing one or more feed streams into the carbonylation reactor, at least one feed stream comprising water; C) measuring a concentration of one or more components in at least one feed stream and/or in the reactor mixture by Raman spectroscopic analysis or by infrared spectroscopic analysis; and D) adjusting at least one feed stream comprising water in response to the concentration measured by Raman spectroscopic analysis or infrared spectroscopic analysis.

One or more embodiments include the process of the preceding paragraph, wherein the concentration is of methanol in a feed stream, and/or methyl acetate in a feed stream, or wherein the concentration is of methyl acetate in the reactor mixture, wherein at least one feed stream comprises methyl acetate, and wherein a conversion rate for methyl acetate is calculated from the concentration of methyl acetate in the reactor mixture and the methyl acetate feed rate.

One or more embodiments include the process of any preceding paragraph, wherein the reactor mixture comprises carbon dioxide, methane, and/or hydrogen.

One or more embodiments include the process of any preceding paragraph, wherein the concentration is of carbon dioxide, methane, and/or hydrogen in the reactor mixture.

One or more embodiments include the process of any preceding paragraph, wherein the adjusting of the feed stream comprising water achieves or maintains water in the reactor mixture in a concentration of about 2 wt % to about 14 wt %.

One or more embodiments include the process of any preceding paragraph, wherein the adjusting is of a feed rate of a feed stream comprising water, and/or wherein the adjusting is of a water make-up feed stream by increasing or decreasing the concentration of water in the water make-up feed stream.

One or more embodiments include the process of any preceding paragraph, wherein the reactor mixture further comprises hydrogen iodide, and optionally comprises methyl acetate, water, carbon dioxide, methyl iodide, and acetic acid.

One or more embodiments include the process of any preceding paragraph, wherein the reactor mixture further comprises a phosphine oxide.

One or more embodiments include the process of any preceding paragraph, wherein the reactor mixture further comprises methyl acetate.

One or more embodiments of the method for producing acetic acid, wherein the reactor mixture further comprises a catalyst stabilizer and/or a catalyst promoter, optionally wherein the catalyst stabilizer is a pentavalent Group VA oxide and/or the catalyst promoter is methyl iodide.

One or more embodiments of the preceding paragraph, wherein the pentavalent Group VA oxide is a phosphine oxide, and/or wherein when the catalyst promoter is methyl iodide, the reactor mixture further comprises methyl acetate, carbon dioxide, and acetic acid.

In another general embodiment, the present disclosure provides a method for measuring a concentration of one or more components in a feed stream comprising methyl acetate and methanol to a carbonylation reactor, which method comprises: a) combining, in the carbonylation reactor, a carbonylation catalyst, methanol, carbon monoxide, and water, to form a reactor mixture; b) introducing a feed stream comprising methyl acetate and methanol into the carbonylation reactor, and c) measuring a concentration of methyl acetate and/or methanol in the feed stream by Raman spectroscopic analysis or by infrared spectroscopic analysis.

One or more embodiments of the preceding paragraph, wherein the concentration of methyl acetate in the feed stream is measured, and/or wherein the feed stream has a methyl acetate:methanol weight ratio from about 90:10 to about 10:90, often from about 60:40 to about 40:60.

One or more embodiments of the method for measuring a concentration of one or more components in a feed stream comprising methyl acetate and methanol to a carbonylation reactor, wherein the method further comprises adjusting at least one feed stream comprising water in response to the concentration measured by Raman spectroscopic analysis or infrared spectroscopic analysis.

One or more embodiments of the preceding paragraph, wherein the adjusting is of a feed rate of a feed stream comprising water, and/or wherein the adjusting is to a water make-up feed stream, and wherein the adjusting is by increasing or decreasing the concentration of water in the water make-up feed stream and/or wherein the adjusting of the feed stream comprising water achieves or maintains water in the reactor mixture in a concentration of about 2 wt % to about 14 wt %.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

DESCRIPTION OF THE DRAWINGS

Further details will be apparent from the following detailed description, with reference to the enclosed drawings, in which.

DETAILED DESCRIPTION OF THE INVENTION

Figure 1:
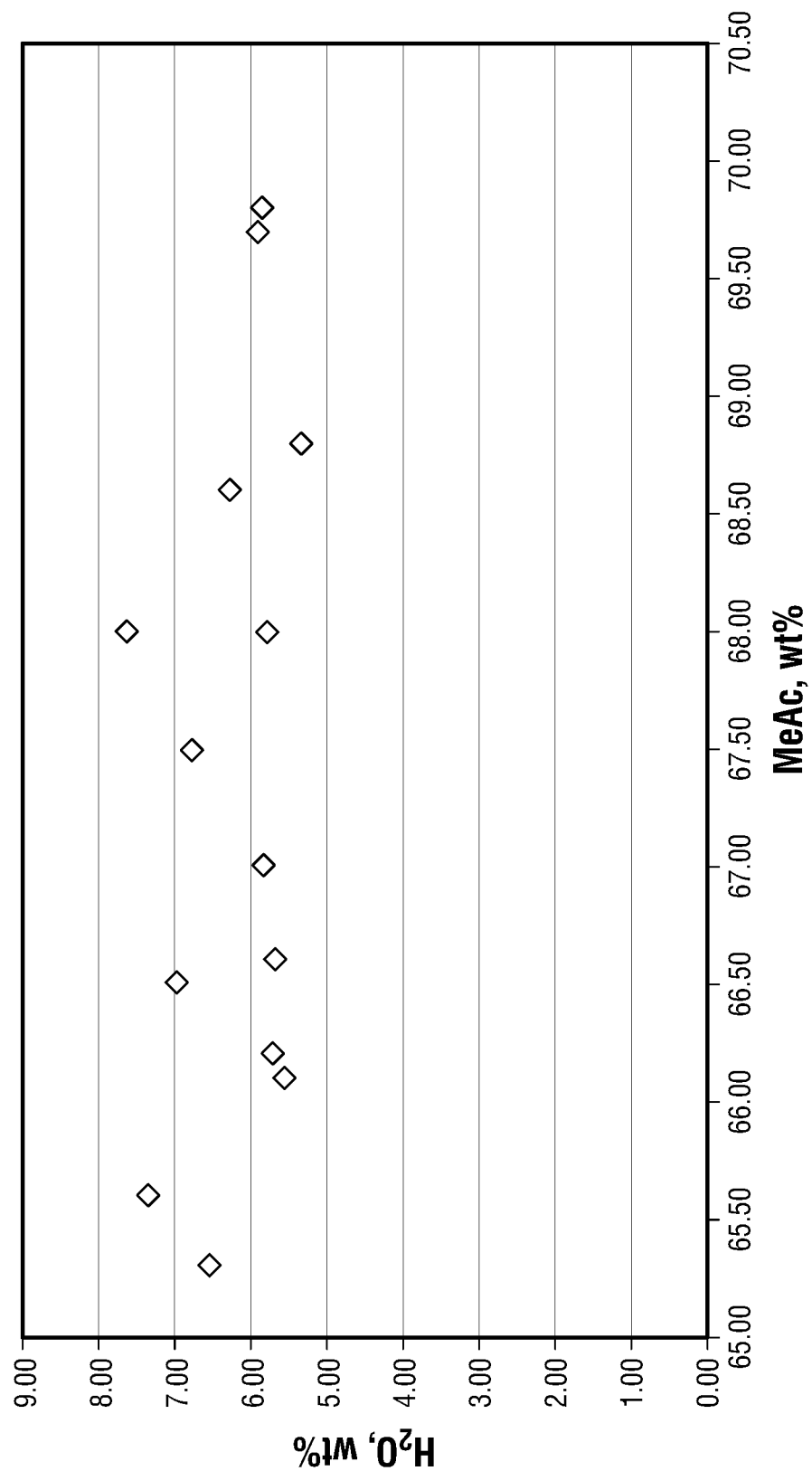
FIG. 1 is a graph showing methyl acetate feed concentrations and corresponding reactor $H_2O$ concentrations for a portion of a 15-day period when the MeAc/MeOH feed and the reactor were sampled once daily.

The present disclosure now will be described more fully hereinafter. However, this technology may be embodied in many different forms and should not be construed as limited to the embodiments set forth herein; rather, these embodiments are provided so that this disclosure will satisfy applicable legal requirements. As such, it will be apparent to those skilled in the art that the embodiments may incorporate changes and modifications without departing from the general scope of the disclosure. It is intended to include all such modifications and alterations in so far as they come within the scope of the appended claims or the equivalents thereof.

As used in this specification and the claims, the singular forms "a," "an," and "the" include plural referents unless the context clearly dictates otherwise.

As used in this specification and the claims, the terms "comprising," "containing," or "including" mean that at least the named compound, element, material, particle, method step, etc., is present in the composition, the article, or the method, but does not exclude the presence of other compounds, elements, materials, particles, method steps, etc., even if the other such compounds, elements, materials, particles, method steps, etc., have the same function as that which is named, unless expressly excluded in the claims. It is also to be understood that the mention of one or more method steps does not preclude the presence of additional method steps before or after the combined recited steps or intervening method steps between those steps expressly identified.

Moreover, it is also to be understood that the lettering of process steps or ingredients is a convenient means for identifying discrete activities or ingredients and the recited lettering can be arranged in any sequence, unless expressly indicated.

For the purpose of the present description and of the claims which follow, except where otherwise indicated, all numbers expressing amounts, quantities, percentages, and so forth, are to be understood as being modified in all instances by the term "about". Also, all ranges include any combination of the maximum and minimum points disclosed and include any intermediate ranges therein, which may or may not be specifically enumerated herein.

All tubing, valving and the like contacting the reaction solution must be chemically inert to the reaction components and be capable of withstanding corrosive attack under reaction conditions. Suitable manufacturing materials for use in the tubes, valves, and similar equipment include HASTELLOY™ B2 Ni—Mo—Fe alloy, HASTELLOY™ B3 Ni—Mo—Fe alloy and zirconium.

Some embodiments include production of glacial acetic acid, which is encompassed by the term "acetic acid" as used herein. Glacial acetic acid generally refers to acetic acid that is undiluted, generally meaning that the acetic acid has a water concentration of about 0.15 wt % or less, based on the total weight of acetic acid and water.

In several embodiments, acetic acid is produced from methanol and carbon monoxide by methanol carbonylation in the presence of water. This is accomplished at least in part by combining, in a carbonylation reactor, a carbonylation catalyst, methanol, carbon monoxide, and water, to form a reactor mixture. One or more feed streams is introduced into the carbonylation reactor, at least one feed stream comprising water. Such carbonylation processes can use carbonylation catalyst systems based on (a) rhodium or (b) iridium, with or without a catalyst stabilizer or a catalyst promoter.

When the catalyst is based on rhodium, the catalyst can be rhodium metal or a rhodium compound. The rhodium compounds can be selected from the group consisting of rhodium salts, rhodium oxides, rhodium acetates, organo-rhodium compounds, coordination compounds of rhodium and mixtures thereof. Specific examples of rhodium compounds include $Rh_2(CO)_4I_2$, $Rh_2(CO)_4Br_2$, $Rh_2(CO)_4Cl_2$, $Rh(CH_3CO_2)_2$, $Rh(CH_3CO_2)_3$ and $[H]Rh(CO)_2I_2$.

When the catalyst is based on iridium, the catalyst can be iridium metal or an iridium compound. The iridium compounds can be selected from the group consisting of iridium salts, iridium oxides, iridium acetates, iridium oxalates, iridium acetoacetates, coordination compounds of iridium and mixtures thereof. Specific examples of iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(Ac)_3$, $[Ir_3O(OAc)_6(H_2O)_3][OAc]$ and $H_2[IrCl_6]$.

In general, there are two types of catalyst stabilizers. The first type of catalyst stabilizer is metal iodide salt such as lithium iodide. The second type of catalyst stabilizer is a non-salt stabilizer, including pentavalent Group VA oxides such as phosphine oxides (e.g., triphenyl phosphine oxide).

An example of a catalyst promoter is methyl iodide. Methyl iodide may be added directly to the process or generated by adding hydrogen iodide to the process.

In the method for producing acetic acid, methanol and carbon monoxide are fed to the carbonylation reactor. In some embodiments, a methyl acetate feed stream is a co-feed to the carbonylation reactor. As an alternative to co-feeding methyl acetate, a mixture of methyl acetate and methanol is a feed stream, often from a byproduct stream of a hydrolysis/methanolysis of polyvinyl acetate, as a co-feed to the carbonylation reactor. In feed streams containing a mixture of methyl acetate and methanol, the feed streams usually have a methyl acetate:methanol weight ratio from about 90:10 to about 10:90, often from about 85:15 to about 15:85; in some embodiments, the methyl acetate:methanol weight ratio is from about 60:40 to about 40:60, often from about 65:35 to about 35:65. Additionally, methyl acetate may be generated in the reactor mixture during the process.

It is believed that the methanol does not react directly with the carbon monoxide to form acetic acid. Instead, it is first converted to methyl acetate by reaction with acetic acid; water is also formed in this reaction. Subsequently, methyl acetate is converted to methyl iodide by hydrogen iodide present in the acetic acid reactor mixture. Methyl iodide then reacts with carbon monoxide and water to give acetic acid and regenerate the hydrogen iodide. The presence of water ensures formation of acetic acid, as water is used in the final step of the catalytic process. Dissolved carbon monoxide assists in catalyst regeneration.

The components in the reactor mixture can include methyl acetate, a catalyst stabilizer, a catalyst promoter and/or hydrogen iodide. The reactor mixture often comprises the carbonylation catalyst, methanol, methyl acetate, water, carbon monoxide, carbon dioxide, methyl iodide, and/or acetic acid.

The carbonylation reaction is performed in the presence of water. In some embodiments, the concentration of water present is from about 2 wt % to about 14 wt %, based on the total weight of the reaction medium. In other embodiments, the water concentration is from about 2 wt % to about 10 wt %. In still other embodiments, the water concentration is from about 4 wt % to about 8 wt %. In some embodiments, a steady-state concentration of water is achieved or maintained. To achieve or maintain the desired water concentration in the reactor mixture in the desired range, a water-containing feed stream to the carbonylation reactor is adjusted.

In embodiments in which methyl acetate is a co-feed with methanol in the same feed stream, it is useful to measure the concentration of the methyl acetate in the feed stream so that the amount of water being fed to the reactor can be adjusted accordingly. In some embodiments, knowledge of methyl acetate concentration in reactor feed permits maintaining a steady state $H_2O$ concentration in the reactor. Methanol undergoes esterification with acetic acid nearly instantly when it enters the reactor to produce $H_2O$ as shown in the equation below.

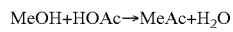

As one mole of $H_2O$ is consumed in methanol carbonylation, there is an approximate balance between $H_2O$ produced via methanol esterification and $H_2O$ consumed during subsequent formation of acetic acid. Methyl acetate does not undergo a similar reaction. To the extent that methyl acetate replaces methanol in the feed stream, to maintain a constant or steady-state $H_2O$ concentration, one mole of $H_2O$ is added to the reactor per mole of methyl acetate added. Without this $H_2O$ balance, there may be swings in reactor $H_2O$ concentration, which usually lead to an unwanted increase in the amount of water consumed by the water gas shift reaction, CO usage inefficiency and/or catalyst instability.

Normally, as the amount of methyl acetate in the combined methyl acetate/methanol (MeAc/MeOH) feed stream increases, the amount of water being fed is increased; similarly, as the amount of methyl acetate in the combined feed stream decreases, the amount of water being fed is decreased. In a particular embodiment, the concentration of methyl acetate and the methyl acetate feed rate are used to calculate a conversion rate for methyl acetate, and the water feed stream is adjusted based on the methyl acetate conversion ratio rather than the concentration value.

In other embodiments, one or more components in the reactor mixture are measured instead of or in addition to the concentration of one or more components in a feed stream, which reactor mixture components can include carbon dioxide, methane, and/or hydrogen.

In some embodiments, the water feed is a water make-up feed stream. In other embodiments, the water feed includes a fresh water feed stream and a water make-up feed stream; one or both of these water feeds can be adjusted.

Examples of adjustments to a feed stream comprising water include increasing or decreasing the feed rate of the feed. In a feed stream in which water is not the only component, the concentration of water in the feed stream can be increased or decreased. An example of a feed stream in which water is not the only component is a water make-up feed stream. Such adjustments can affect the concentration of water in the reactor mixture and obtain (achieve) or maintain the water concentration in the reactor mixture within a desired range.

The carbonylation reaction can be performed at a temperature within the range of about 150 degrees Celsius (° C.) to about 250° C. and under a pressure within the range of about 200 psig (1380 kPa) to about 2,000 psig (13,800 kPa).

After the carbonylation reaction, the reaction mixture is passed downstream to separation units. Separations unit may be defined herein as a vessel or step in an acetic acid process which separates a feed stream into two or more separate exit streams where the two exit streams differ from one another in some aspect. The separation can be based on methods such as separation by physical characteristics (e.g., density, volatility, boiling point, phase, absorbance, and adsorbance) and other characteristics used for separating chemical components.

The separation units can include, but are not limited to, a flash tank, a light ends distillation column, a decanter, a drying column, and a heavy ends distillation column.

In a flash tank, the acetic acid product stream is withdrawn from the reactor and separated into (a) a liquid fraction containing the catalyst and the catalyst stabilizer and (b) a vapor fraction containing the acetic acid product, the reactants, water, methyl iodide, and impurities generated during the carbonylation reaction including acetaldehyde. The liquid fraction can be recycled to the carbonylation reactor. The vapor fraction is then passed to a distillation column.

In a light ends distillation column, the vapor fraction is separated based upon boiling point into at least (a) an overhead fraction containing methyl iodide, water, methanol, methyl acetate, acetic acid, alkanes and acetaldehyde and (b) an acetic acid stream containing acetic acid, water, hydrogen iodide and heavy impurities such as propionic acid.

In a decanter, the overhead fraction is condensed and separated by density to (a) a lighter aqueous phase and (b) a heavier organic phase. The lighter aqueous phase can contain water, acetic acid, methyl acetate, methyl iodide, acetaldehyde and alkanes and have a density of about 1.0 grams per cubic centimeter to about 1.10 grams per cubic centimeter. Like the lighter aqueous phase, the heavier organic phase can contain water, acetic acid, methyl acetate, methyl iodide, acetaldehyde and alkanes; the organic phase may further comprise higher concentrations of methyl iodide and alkanes. The heavier organic phase can have a density of about 1.4 grams per cubic centimeter to about 2.2 grams per cubic centimeter. The lighter aqueous phase can be recycled to the reactor or to the light ends distillation column.

In a drying column, the residual water is removed from the acetic acid stream. In a heavy ends distillation column, the heavy impurities are removed from the acetic acid stream.

In a general embodiment, the present disclosure provides a method for measuring the concentration of one or more components in a feed stream and/or in the reactor mixture of the acetic acid process by infrared and/or Raman spectroscopic analyses and then adjusting at least one feed stream comprising water in response to the measured concentration. In some embodiments, a method for measuring the various acetic acid stream components is performed using an online infrared or Raman spectroscopy method, which permits the method to be performed instantly or in real time.

Infrared spectroscopy can measure rhodium, dissolved carbon dioxide, water, acetic acid, hydrogen iodide, methyl iodide, methyl acetate, and triphenyl phosphine oxide, while Raman spectroscopy can measure water, acetic acid, hydrogen iodide, methyl iodide, methyl acetate, acetaldehyde, triphenyl phosphine oxide and dissolved carbon monoxide.

Another embodiment provides a method for measuring a concentration of one or more components in a feed stream comprising methyl acetate and methanol to a carbonylation reactor by measuring a concentration of methyl acetate and/or methanol in the feed stream by Raman spectroscopic analysis or by infrared spectroscopic analysis. The methyl acetate and/or methanol concentration in the feed stream can be measured. This method often further comprises adjusting at least one feed stream comprising water in response to the concentration measured by Raman spectroscopic analysis or infrared spectroscopic analysis. The desired water concentrations in the reactor mixture are as described above. Water feed streams and adjustments thereto are as described above.

In various embodiments, an attenuated total reflectance (ATR) probe can be used to monitor a feed stream or a reactor mixture. Alternatively, a reactor slipstream can pass through an infrared analyzer equipped with a flow-through ATR cell or flow-through transmission cell. In the case of a slipstream, continuous flow can be employed, and the feed stream or reactor mixture can be returned to the reaction system. Instead of a probe, a flow through cell equipped with windows may also be used to monitor a slipstream. The use of a back pressure regulator or similar device can prevent a pressure drop across the cells, thereby ensuring analyses are performed with minimal change from the reactor pressure and there is no degassing or bubble formation in the cells. A light signal from the reactor solution can be transferred to a detector by light pipe, chalcogenide fiber or other methods.

The temperature of the slipstream can be maintained anywhere between ambient and process temperature. Selection of the temperature depends on several parameters, such as precipitation of solids, compatibility of the cell window or crystal materials with process conditions and controlling the process reaction in the slipstream.

Depending on the temperature employed, the cell window or crystal material can be selected from the group consisting of $CaF_2$, ZnS, sapphire, AMTIR (Se—Ge—As composite), Ge, ZnSe, Si, diamond, KRS-5 (thallium bromoiodide) and cubic zirconia. While in no way limiting the scope of the technology, sapphire is desirable in some embodiments because it has the appropriate transmission range to allow certain analyses to be performed and displays good mechanical strength, chemical resistance and resistance to etching in the process.

The monitoring (measuring) of one or more feed stream components and/or reaction mixture components in accordance with the present technology can be carried out by analyzing a combination of select spectral ranges of traditional mid (400-4000 $cm^{-1}$), extended mid (4000-7000 $cm^{-1}$) and near (4000-12000 $cm^{-1}$) infrared (IR) regions. In some embodiments, Fourier transform infrared (FT-IR) spectroscopic analysis is performed.

One option for monitoring acetic acid reactor mixture components and/or feed stream components involves the use of a dual transmission cell, dual detector setup in which the reactor mixture sequentially flows through both cells. These cells differ only in path length. In some embodiments, one cell may have a path length of 0.05-0.20 mm, which allows for analysis in the spectral region between 1800 and 5600 $cm^{-1}$ and thereby encompasses portions of traditional mid- and extended mid-infrared regions. The second cell, in certain embodiments, may have a path length of 0.2-5.0 mm, which allows for analysis in either the extended mid-infrared region or the near-infrared region. The different cell path lengths can be utilized to counteract the highly absorbing nature of acetic acid and take advantage of the two different spectroscopic regions for reaction mixture component characterization.

Alternatively, a single transmission cell and single detector setup can be used. For example, a cell with a path length of 0.2-5.0 mm can be used for the near-infrared region. Another possible cell may have, in some embodiments, a shorter path length of 0.05-0.20 mm, which can be used for the "non-fingerprint" region (i.e., 1800-5600 $cm^{-1}$). Yet another possible cell may have, in some embodiments, a much shorter path length of 0.005 to 0.015 mm, which allows for coverage of both the non-fingerprint region and the fingerprint region (i.e., 1800-400 $cm^{-1}$). This shorter path length can also be effectively achieved by using an attenuated total reflectance (ATR) crystal rather than a transmission cell.

Drawbacks regarding the use of infrared spectroscopy include large $H_2O$ absorbance values, large acetic acid absorbance values, relatively weak methyl iodide absorbance values, and the tendency of $H_2O$ and acetic acid absorbance values to overlap and interfere with the absorbance of other components. These factors make calibration for methyl iodide and methyl acetate less accurate and may adversely affect quantitation of detectable species.

Additionally, a large number of calibration standards are usually needed for acetic acid processes to obtain calibration models with acceptable accuracy. Moreover, infrared spectroscopy has drawbacks regarding hardware flexibility and implementation in a process environment.

Another method for measuring the various components in a feed stream and/or the reactor mixture is online Raman spectroscopy. Like the infrared method, this Raman method provides measurements that can be used to adjust a feed stream comprising water. A Raman shift occurs when light impinges upon a molecule and interacts with the electron cloud and the bonds of that molecule. It is believed that a photon excites the molecule from the ground state to a virtual energy state and that when the molecule relaxes, the molecule emits a photon and returns to a different rotational or vibrational state. The difference in energy between the original state and the new state leads to a shift in the emitted photon's frequency away from the excitation wavelength.

Raman spectra can be shown as plots of signal strength or peak intensity (arbitrary units) versus Raman shift. Raman shifts can be expressed in wavenumbers, which have units of inverse length such as inverse centimeters ($cm^{-1}$).

The instrumentation used to collect and process Raman data includes a Raman spectrometer system, a transmittance system, a control loop and a processor. The Raman spectrometer system comprises a Raman spectrometer, with its principal components being a light source, a monochromator and a detector. The light source delivers excitation radiation to the probe, where scattered radiation is collected, filtered of Raleigh scattered light and dispersed via a monochromator. The dispersed Raman scattered light is then imaged onto a detector and subsequently processed within the processor.

The light source can be a visible laser, such as a frequency-doubled Nd:YAG laser (532 nm), a helium-neon laser (633 nm) or a solid-state diode laser (785 nm). The laser can be pulsed or continuous wave (CW), polarized as desired or randomly polarized, or single-mode. Light sources other than lasers can be used. The excitation radiation can be delivered to the probe, and the scattered radiation can be collected from the probe.

The collected scattered radiation is filtered to remove Raleigh scattering and frequency (wavelength) dispersed using a suitable dispersive element or interferometrically. The monochromator can be any such dispersive element, along with associated filters and beam manipulation optics. The dispersed Raman scattering is imaged onto a detector. Detectors can include array detectors or single element detectors. In the case of array detectors, the detector is calibrated such that the frequency (wavelength) corresponding to each detector element is known. The detector response is delivered to the processor that generates a set of frequency shift, intensity (x,y) data points which constitute the Raman spectrum. Raman spectroscopy can measure water, acetic acid, hydrogen iodide, methyl iodide, methyl acetate, acetaldehyde, pentavalent phosphine oxides such as triphenyl phosphine oxide and a mixture of four trialkyl phosphine oxides in which the alkyl groups are n-hexyl and n-octyl (Cytop® 503; formerly Cyanex® 923; Cytec Industries, Inc.), and dissolved carbon monoxide.

Moreover, Raman spectroscopy permits the calculation of accurate methyl iodide and methyl acetate concentrations. Notably, methyl iodide has a strongly-scattering, characteristic peak in the Raman spectrum, with imperceptibly low interference from any other reactor solution components. Additionally, water and acetic acid Raman peaks permit accurate determination of their concentrations without interfering with peaks for methyl iodide or methyl acetate. In addition, pentavalent phosphine oxides, which include triphenyl phosphine oxide (TPPO) and Cytop® 503, can also be accurately measured by Raman spectroscopy.

The scattered radiation of the carbonylation reaction mixture may be collected by a probe in a variety of locations in one or more of the separations units. The probe may be placed directly in a vessel, a feed stream entering or exiting the unit or a slipstream. Alternatively, the probe may be situated so as not to contact a liquid mixture.

EXAMPLES

The following example is included to demonstrate certain embodiments of the technology. It should be appreciated by those of skill in the art that many changes can be made in the specific embodiments described herein and still obtain similar results without departing from the spirit and scope of the disclosure.

Data in the following Example were obtained from a continuous methanol carbonylation unit equipped with a reactor, a flash tank, a light ends distillation column, a decanter and a drying column. A methyl acetate/methanol feed obtained from a polyvinyl alcohol (PVA) process was fed to the reactor. During a 34-day run, the unit was first allowed to reach steady state operation over a period of about 5 days. For the first 15 days of the remaining 29 days of run time, the methyl acetate/methanol feed was sampled about once daily for GC analysis. Over the final 14 days, the methyl acetate/methanol feed was sampled every 4 hours for analysis. Over the whole 29-day steady-state period, the reactor was sampled every 4 hours and $H_2O$ analysis was carried out.

Table 1 below shows methyl acetate feed concentrations and corresponding reactor $H_2O$ concentrations for a portion of the 15-day period (129 to 511 hours) when MeAc/MeOH feed and the reactor were sampled once daily; these data are plotted in FIG. 1. Table 2 shows methyl acetate feed concentrations and corresponding reactor $H_2O$ concentrations for a portion of the 14-day period (511 to 819 hours) when both the MeAc/MeOH feed and the reactor water were measured every 4 hours; these data are plotted in FIG. 2.

TABLE 1

| Time | Methyl acetate in feed | $H_2O$ in reactor |
|---|---|---|
| 129 hrs. | 70.50 wt % | 6.33 wt % |
| 149 hrs. | 68.60 wt % | 6.26 wt % |
| 179 hrs. | 68.00 wt % | 7.63 wt % |
| 201 hrs. | 67.50 wt % | 6.78 wt % |
| 225 hrs. | 68.00 wt % | 5.78 wt % |
| 249 hrs. | 69.80 wt % | 5.85 wt % |
| 273 hrs. | 68.80 wt % | 5.35 wt % |
| 297 hrs. | 66.60 wt % | 5.68 wt % |
| 321 hrs. | 67.00 wt % | 5.83 wt % |
| 345 hrs. | 66.50 wt % | 6.97 wt % |
| 369 hrs. | 65.60 wt % | 7.36 wt % |
| 393 hrs. | 65.30 wt % | 6.56 wt % |
| 417 hrs. | 69.70 wt % | 5.91 wt % |
| 441 hrs. | 66.20 wt % | 5.71 wt % |
| 465 hrs. | 66.10 wt % | 5.54 wt % |
| 511 hrs. | 69.80 wt % | 6.54 wt % |

TABLE 2

| Time | Methyl acetate in feed | $H_2O$ in reactor |
|---|---|---|
| 645 hrs. | 67.80 wt % | 6.38 wt % |
| 649 hrs. | 67.90 wt % | 6.33 wt % |
| 653 hrs. | 67.90 wt % | 5.83 wt % |
| 657 hrs. | 67.80 wt % | 5.54 wt % |
| 661 hrs. | 68.90 wt % | 5.88 wt % |
| 665 hrs. | 68.90 wt % | 5.94 wt % |
| 669 hrs. | 69.10 wt % | 5.84 wt % |
| 673 hrs. | 69.70 wt % | 5.89 wt % |
| 677 hrs. | 69.50 wt % | 6.33 wt % |
| 681 hrs. | 69.90 wt % | 5.90 wt % |
| 685 hrs. | 69.70 wt % | 6.04 wt % |
| 689 hrs. | 70.00 wt % | 6.21 wt % |

Figure 2:
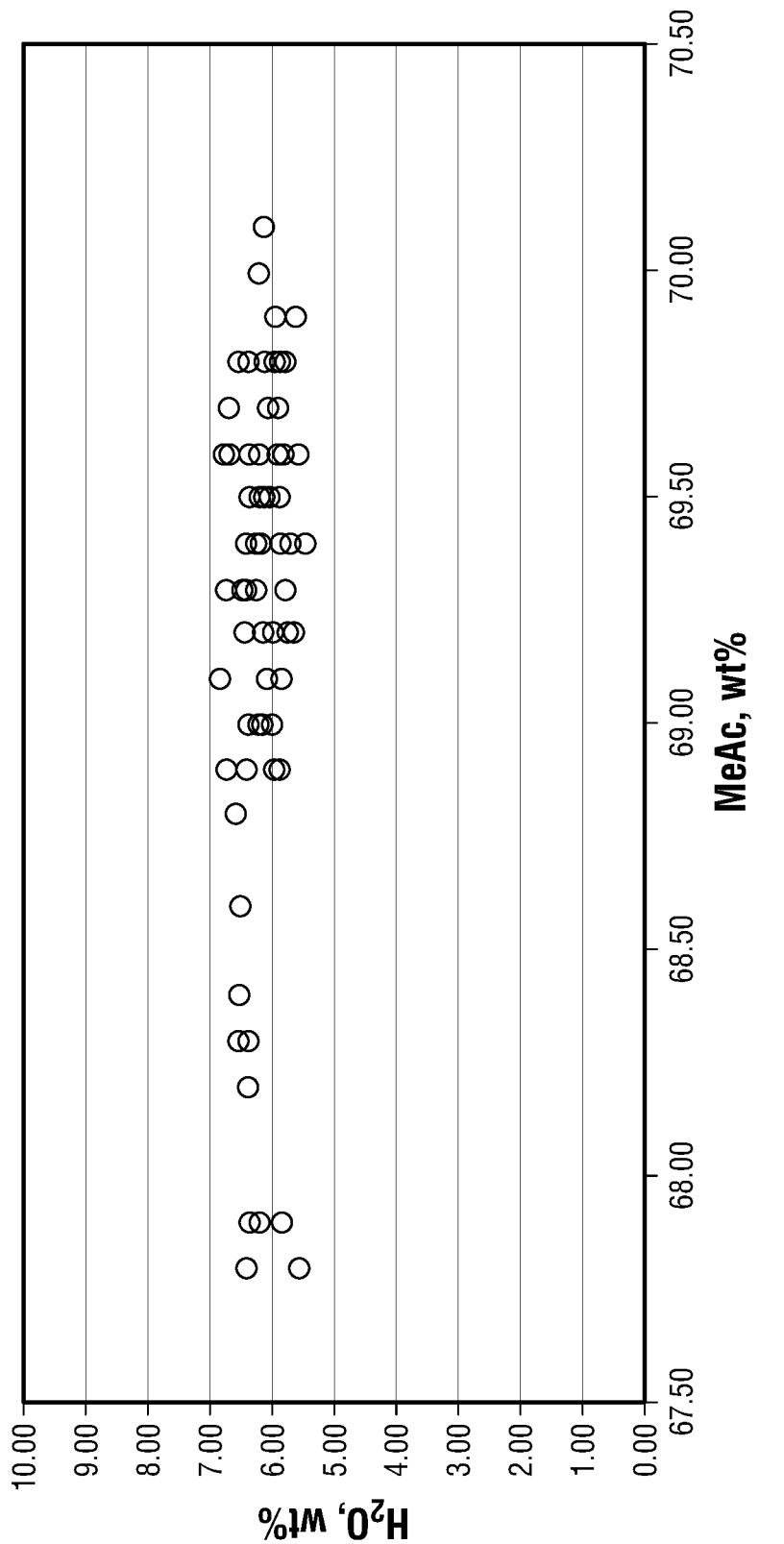
FIG. 2 is a graph showing methyl acetate feed concentrations and corresponding reactor $H_2O$ concentrations for a portion of a 14-day period when both the MeAc/MeOH feed and the reactor $H_2O$ were measured every 4 hours.

It can be observed from Table 2 and FIG. 2 that more frequent analysis of the methyl acetate feed allows, in response, more frequent adjustments of the reactor $H_2O$ concentration (such as by increasing or decreasing make-up $H_2O$ feed), which in turn leads to better control of the reactor $H_2O$ concentration, as compared to less frequent analysis of the methyl acetate feed.

Figure 3:
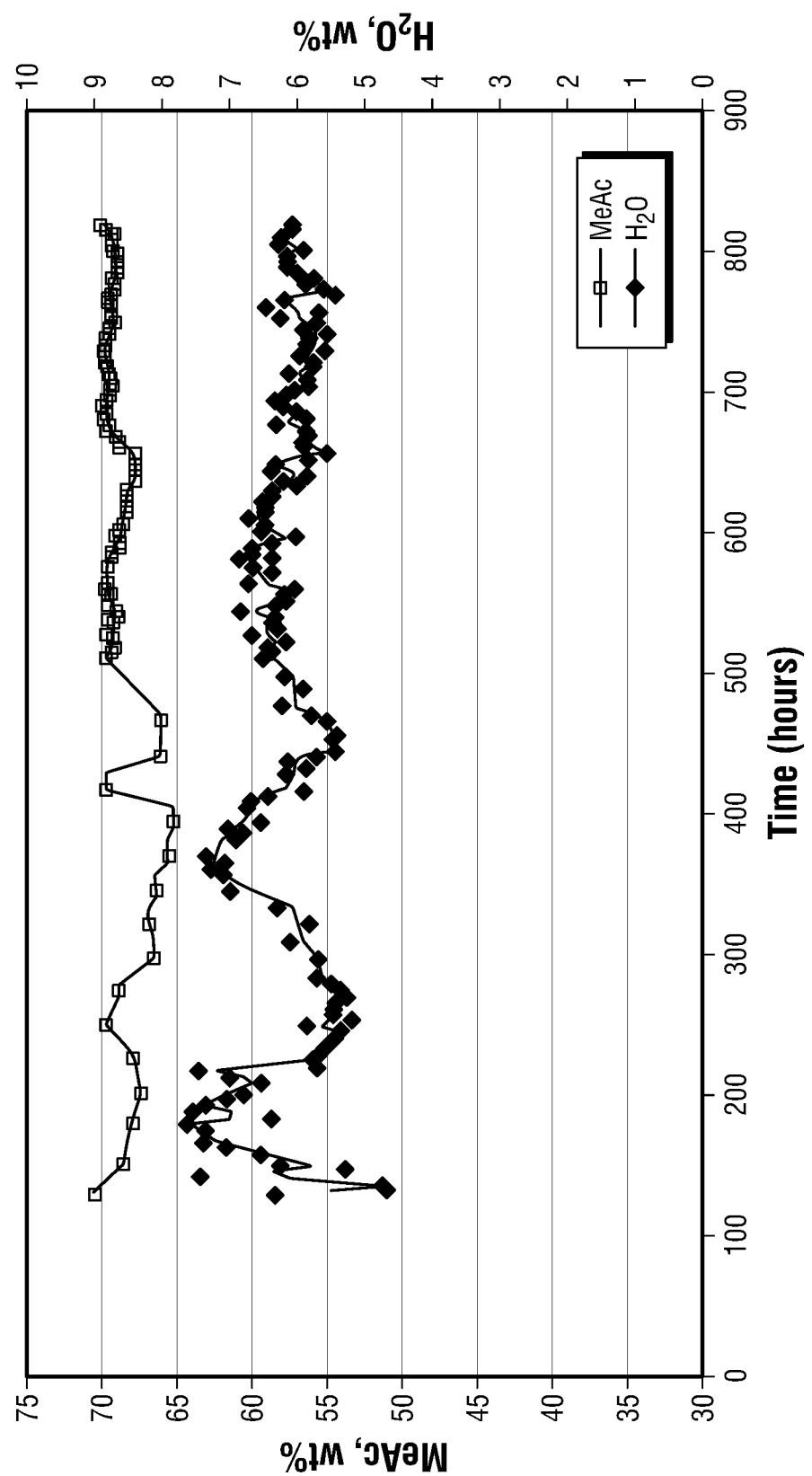
FIG. 3 is a graph showing profiles for methyl acetate in the MeAc/MeOH feed and reactor $H_2O$ concentration for the 29-day period encompassing FIGS. 1 and 2.

The profiles for methyl acetate in the MeAc/MeOH feed and reactor $H_2O$ concentration for the entire 29-day period are shown in FIG. 3.

Although the present technology and its advantages have been described in detail, it should be understood that various changes, substitutions and alterations can be made herein without departing from the spirit and scope of the technology as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods and/or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods and/or steps.

What is claimed is:

1. A method for controlling an acetic acid production process comprising:
   A) combining, in a carbonylation reactor, a carbonylation catalyst, methanol, carbon monoxide, and water, to form a reactor mixture;
   B) introducing one or more feed streams into the carbonylation reactor, wherein at least one feed stream comprising water, and at least one feed stream comprising methanol and methyl acetate, wherein the feed stream comprising methanol and methyl acetate has a methyl acetate:methanol weight ratio from about 90:10 to about 10:90;
   C) measuring the concentration of one or more components in at least one feed stream and/or in the reactor mixture by Raman spectroscopic analysis or by infrared spectroscopic analysis; and
   D) adjusting at least one feed stream comprising water in response to the concentration measured by Raman spectroscopic analysis or infrared spectroscopic analysis.

2. The method of claim 1, wherein the concentration is of methanol in a feed stream and/or methyl acetate in a feed stream.

3. The method of claim 1, wherein the concentration is of methyl acetate in the reactor mixture, and wherein the conversion rate for methyl acetate from acetic acid is calculated from the concentration of methyl acetate in the reactor mixture and the methyl acetate feed rate.

4. The method of claim 1, wherein the reactor mixture comprises carbon dioxide, methane, and/or hydrogen.

5. The method of claim 1, wherein the concentration is of carbon dioxide, methane, and/or hydrogen in the reactor mixture.

6. The method of claim 1, wherein the adjusting of the feed stream comprising water achieves or maintains water in the reactor mixture in a concentration of about 2-14 wt %.

7. The method of claim 1, wherein the adjusting is of a feed rate of a feed stream comprising water, and/or wherein the adjusting is to a water make-up feed stream by increasing or decreasing the concentration of water in the water make-up feed stream.

8. The method of claim 1, wherein the reactor mixture further comprises hydrogen iodide, and optionally comprises, carbon dioxide, methyl iodide, and acetic acid.

9. The method of claim 8, wherein the reactor mixture further comprises a phosphine oxide.

10. The method of claim 8, wherein the reactor mixture further comprises methyl iodide and acetic acid.

11. The method of claim 1, wherein the reactor mixture further comprises a catalyst stabilizer and/or a catalyst promoter, optionally wherein the catalyst stabilizer is a pentavalent Group VA oxide and/or the catalyst promoter is methyl iodide.

12. The method of claim 11, wherein the pentavalent Group VA oxide is a phosphine oxide.

13. The method of claim 11, wherein when the catalyst promoter is methyl iodide, the reactor mixture further comprises methyl acetate, carbon dioxide, and acetic acid.

14. A method for controlling an acetic acid production process comprising:
   a) combining, in a carbonylation reactor, a carbonylation catalyst, methanol, carbon monoxide, and water, to form a reactor mixture;
   b) introducing a feed stream comprising methyl acetate and methanol into the carbonylation reactor, wherein the feed stream has a methyl acetate:methanol weight ratio from about 90:10 to about 10:90, and
   c) measuring the concentration of methyl acetate and/or methanol in the feed stream by Raman spectroscopic analysis or by infrared spectroscopic analysis.

15. The method of claim 14, wherein the concentration of methyl acetate in the feed stream is measured.

16. The method of claim 14, wherein the feed stream has a methyl acetate:methanol weight ratio from about 85:15 to about 15:85.

17. The method of claim 14, wherein the feed stream has a methyl acetate:methanol weight ratio from about 60:40 to about 40:60.

18. The method of claim 14, which further comprises adjusting at least one feed stream comprising water in response to the concentration measured by Raman spectroscopic analysis or infrared spectroscopic analysis.

19. The method of claim 18, wherein the adjusting is of a feed rate of the feed stream comprising water, and/or wherein the adjusting is to a water make-up feed stream, and wherein the adjusting is by increasing or decreasing the concentration of water in the water make-up feed stream.

20. The method of claim 18, wherein the adjusting of the feed stream comprising water achieves or maintains water in the reactor mixture in a concentration of about 2-14 wt %.

* * * * *